United States Patent
De Nanteuil et al.

(10) Patent No.: US 6,288,077 B1
(45) Date of Patent: Sep. 11, 2001

(54) 2,3-METHANO-AMINO ACID COMPOUNDS

(75) Inventors: Guillaume De Nanteuil, Suresnes; Philippe Gloanec, Bougival; Tony Verbeuren, Vernouillet; Alain Rupin, Savonnieres, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/561,618

(22) Filed: May 2, 2000

(30) Foreign Application Priority Data

May 3, 1999 (FR) .................................................. 99 05601

(51) Int. Cl.[7] .................. A61K 31/435; A61K 31/40; C07D 221/04; C07D 209/52
(52) U.S. Cl. .................. 514/299; 514/412; 514/414; 546/112; 548/452; 548/465
(58) Field of Search ..................... 514/299, 412, 514/414; 546/112; 548/452, 465

(56) References Cited

U.S. PATENT DOCUMENTS

| | | | |
|---|---|---|---|
| 4,954,158 | * | 9/1990 | Stammer .................................. 71/76 |
| 5,688,826 | * | 11/1997 | Massey et al. ........................ 514/443 |
| 6,110,930 | * | 8/2000 | Taniguchi et al. ................... 514/299 |

OTHER PUBLICATIONS

Switzer et al. "Synthesis of (+−)−2,3,−methanoproline:a novel inhibitor of ethylene biosynthesis" CA 112:217486, 1989.*

* cited by examiner

*Primary Examiner*—Ceila Chang
(74) *Attorney, Agent, or Firm*—The Firm of Hueschen and Sage; G. Patrick Sage

(57) ABSTRACT

Compound of formula (I):

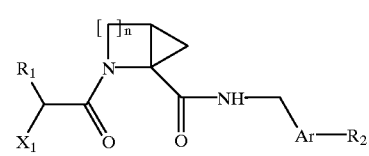

wherein:

n represents 2 or 3, $R_1$ represents optionally substituted alkyl, cycloalkyl or optionally substituted phenyl, $R_2$ represents amino, optionally substituted amidino, optionally substituted guanidino or optionally substituted isothioureido, Ar represents aryl or heteroaryl, $X_1$ represents hydroxy or optionally substituted amino, isomers thereof, and also salts thereof with a pharmaceutically acceptable acid or base, and which medicinal products containing the same/are useful as trypsin-related serine protease inhibitors.

15 Claims, No Drawings

2,3-METHANO-AMINO ACID COMPOUNDS

The present invention relates to new 2,3-methano-amino acid compounds.

BACKGROUND OF THE INVENTION

One of those serine proteases, thrombin, is the key enzyme for coagulation and plays a central role in venous and arterial thrombosis pathology in view, in particular, of its marked ability to cause autoamplification of the coagulation cascade (F. Toti et al, Sang, Thrombose, Vaisseaux 1992, 4, 483–494 and T. M. Reilly et al., Blood Coagulation and Fibrinolysis 1992, 3, 513–517).

The specific and direct inhibition of thrombin is more efficient and presents fewer risks of haemorrhage than treatment with heparin. Direct inhibitors of thrombin do currently exist, but the drawback of such peptide substances is that they are not active when administered by the oral route.

DESCRIPTION OF THE PRIOR ART

Peptidomimetic compounds having an oral antithrombotic activity have already been described in the literature. These include, in particular, the boronic acid compounds described in the patent specifications EP 293 881, EP 471 651, EP 615 978 and EP 792 883 and the compounds described in the patent specifications WO 94 29336 and WO 95 23609.

The synthesis of new serine protease inhibitors for the purpose of increasing the effectiveness and selectivity of the compounds already described in the literature has therefore been of particular interest.

In addition, the new compounds increase various coagulation times and are active when administered by the oral route.

DETAILED DESCRIPTION OF THE INVENTION

More specifically, the present invention relates to compounds of formula (I):

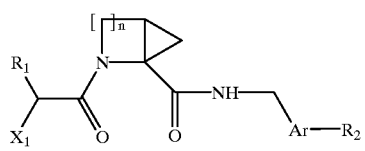

wherein:
n represents 2 or 3,
$R_1$ represents a $(C_3-C_8)$cycloalkyl group, an optionally substituted phenyl group or a linear or branched $(C_1-C_6)$alkyl group optionally substituted by one or more identical or different groups selected from halogen, $(C_3-C_8)$cycloalkyl and optionally substituted phenyl,
$R_2$ represents
  an amino group,
  an amidino group optionally substituted by one or more identical or different groups selected from linear or branched $(C_1-C_6)$alkyl and hydroxy,
  a guanidino group optionally substituted by a linear or branched $(C_1-C_6)$alkyl group, or
  an isothioureido group optionally substituted by a linear or branched $(C_1-C_6)$alkyl group,
Ar represents an aryl group or a monocyclic nitrogen-containing heteroaryl group,
$X_1$ represents a hydroxy group, an amino group or an —$NHR_3$ group,
$R_3$ represents a propargyl group, an iminomethyl group, a linear or branched $(C_1-C_6)$alkylsulphonyl group, a linear or branched aryl$(C_1-C_6)$alkylsulphonyl group, a —$CONR'_3R''_3$ group or a linear or branched $(C_1-C_6)$alkyl group optionally substituted by:
  a —$CO_2R'_3$ group,
  a —$CONR'_3R''_3$ group,
  a heterocyclic group,
  an aminosulphonyl group,
  an aryl group, or
  a heteroaryl group,
    $R'_3$ and $R''_3$, which may be identical or different, each represents a hydrogen atom, or a linear or branched $(C_1-C_6)$alkylsulphonyl group, an aryl group, a linear or branched $(C_1-C_6)$alkyl group (optionally substituted by a carboxy group, a linear or branched $(C_1-C_6)$alkoxycarbonyl group or a carbamoyl group) or form, with the nitrogen atom carrying them, a heterocyclic group, to their isomers, and also to addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid, etc.

Among the pharmaceutically acceptable bases there may be mentioned, without implying any limitation, sodium hydroxide, potassium hydroxide, triethylamine, tert-butylamine, etc.

An optionally substituted phenyl group is to be understood as being substituted by one or more identical of different groups selected from halogen, linear or branched $(C_1-C_6)$alkyl, linear or branched $(C_1-C_6)$alkoxy, hydroxy, linear or branched trihalo-$(C_1-C_6)$alkyl and amino (optionally substituted by one or more linear or branched $(C_1-C_6)$alkyl groups).

A heterocyclic group is to be understood as meaning a saturated or unsaturated, mono- or bi-cyclic group having from 5 to 12 ring members containing one, two or three hetero atoms selected from oxygen, nitrogen and sulphur, it being understood that the heterocycle may be optionally substituted by one or more identical or different groups selected from halogen, linear or branched $(C_1-C_6)$alkyl, linear or branched $(C_1-C_6)$alkoxy, oxo, hydroxy, linear or branched trihalo-$(C_1-C_6)$alkyl groups and amino (optionally substituted by one or more linear or branched $(C_1-C_6)$alkyl groups). Preferred heterocyclic groups are the groups morpholinyl, piperazinyl, piperidyl, dihydrotriazolyl and imidazolinyl.

An aryl group is to be understood as meaning phenyl, biphenylyl or naphthyl, each of those groups being optionally substituted by one or more identical or different groups selected from halogen, linear or branched $(C_1-C_6)$alkyl, linear or branched $(C_1-C_6)$alkoxy, hydroxy, linear or branched trihalo-$(C_1-C_6)$alkyl, amino (optionally substituted by one or more linear or branched $(C_1-C_6)$alkyl groups) and carboxy.

A heteroaryl group is to be understood as meaning an aromatic mono- or bicyclic group having from 5 to 12 ring members containing one, two or three hetero atoms selected from oxygen, nitrogen and sulphur, it being understood that heteroaryl may be optionally substituted by one or more identical or different groups selected from halogen, linear or branched ($C_1$–$C_6$)alkyl, hydroxy, linear or branched ($C_1$–$C_6$) alkoxy, trihalomethyl and amino (optionally substituted by one or more linear or branched ($C_1$–$C_6$)alkyl groups). Of the heteroaryl groups, the following may be mentioned without implying any limitation: thienyl, pyridyl, furyl, pyrrolyl, imidazolyl, oxazolyl, isoxazolyl, thiazolyl, isothiazolyl, pyrimidinyl, pyrazinyl, pyridazinyl, pyrazolyl and quinolyl. Preferred heteroaryl groups are optionally substituted pyridyl and optionally substituted quinolyl groups.

The preferred relative configuration of the 2,3-methano-amino acid group of the compounds of formula (I) is cis ((2R,3S) or (2S,3R)). The preferred absolute configuration of the 2,3-methano-amino acid group of the compounds of formula (1) is (2S,3R).

Preferred $R_1$ groups of formula (I) are cycloalkyl and optionally substituted alkyl groups.

Preferred $R_2$ groups of formula (I) are amino and amidino groups.

The term "aryl" in relation to the group Ar as defined for formula (I) is preferably an optionally substituted phenyl group.

The term "monocyclic nitrogen-containing heteroaryl" in relation to the group Ar as defined for fornula (y) is preferably an optionally substituted pyridyl group.

Preferred $X_1$ groups of formula (I) are amino and —$NHR_3$ groups, wherein $R_3$ represents a linear or branched aryl($C_1$–$C_6$)alkylsulphonyl group or an optionally substituted, linear or branched ($C_1$–$C_6$)alkyl group.

The invention relates also to a process for the preparation of compounds of formula (I) which is characterized in that a compound of formula (II):

(II)

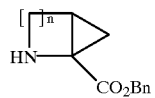

wherein n is as defined for formula (I) and Bn represents a benzyl group, is reacted with a compound of formula (III):

(III)

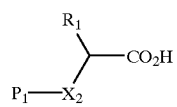

wherein $R_1$ is as defined for formula (I), $X_2$ represents an oxygen atom or —NH—, and $P_1$ represents an amino function-protecting or hydroxy function-protecting group, in the presence of a peptide coupling agent, to yield a compound of formula (IV):

(IV)

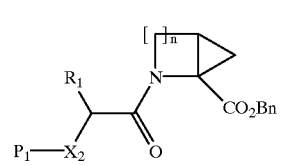

wherein n, $R_1$, $X_2$, Bn and $P_1$ are as defined hereinbefore, which compound of formula (IV) is then converted, by catalytic hydrogenation or by hydrolysis, into a compound of formula (V):

(V)

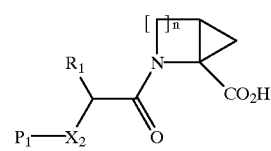

wherein n, $R_1$, $X_2$ and $P_1$ are as defined hereinbefore, which compound of formula (V) is then reacted with a compound of formula (VI):

(VI)

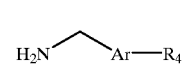

wherein Ar is as defined for formula (I) and $R_4$ represents $R_2$ or $R_2$—$P_2$, $R_2$ being as defined for formula (I) and $P_2$ representing an amino function-protecting group,
in the presence of a peptide coupling agent,
to yield a compound of formula (VII):

(VII)

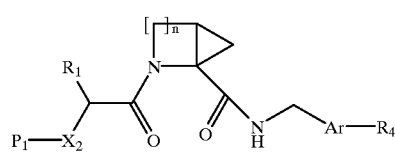

wherein n, $R_1$, $R_4$, Ar, $X_2$ and $P_1$ are as defined hereinbefore,
which compound of formula (VII) is then converted into a compound of formula (I) by one or more deprotection, alkylation or reductive amination reactions,
which compound of formula (I) is purified, if necessary, according to a conventional purification technique, is separated, if desired, into its isomers according to a conventional separation technique, and is converted, if desired, into an addition salt with a pharmaceutically acceptable acid or base.

The compounds of formula (II) are obtained in accordance with the process described by A. Hercouet et al. (Tetrahedron: Asymmetry 1996, Vol. 7 No5, pp. 1267–1268 and Tet. Lett. 1996, Vol. 37 No26, pp. 4529–4532).

In addition to the fact that the compounds of the present invention are new, they have especially valuable pharmacological properties.

They are potent trypsin-related serine protease inhibitors which exhibit a significant selectivity in respect of thrombin compared with other coagulation and fibrinolysis serine proteases.

Those properties thus render them useful in the treatment of stable or unstable angina, disorders of thrombotic origin and/or giving rise to thrombotic complications, in the treatment or prevention of myocardial infarction and venous or arterial thrombosis, and also in the treatment of the complications of vascular and cardiovascular diseases, such as atherosclerosis, arteritis, venous disease and in the treatment of all the disorders which imply thrombin formation and/or activity.

They may equally be used in therapeutic association with a thrombolytic.

The invention extends also to pharmaceutical compositions comprising as active ingredient a compound of formula (I) together with one or more suitable inert, non-toxic excipients. Among the pharmaceutical compositions according to the invention there may be mentioned more especially those which are suitable for oral, parenteral (intravenous or subcutaneous) or nasal administration, tablets or dragees, sublingual tablets, gelatin capsules, lozenges, suppositories, creams, ointments, dermal gels, injectable preparations, drinkable suspensions etc.

The useful dosage can be adapted in accordance with the nature and the severity of the disorder, the administration route and also the age and weight of the patient. That dosage varies from 1 to 500 mg per day taken in one or more administrations.

The following Examples illustrate the invention but do not limit it in any way.

The abbreviations used in the Examples are as follows:
HOBT 1-hydroxybenzotriazole hydrate
TBTU O-(1H-benzotriazol-1-yl)-N,N,N',N'-tetramethyluronium tetrafluoroborate (2S,3R)-2,3-methano-proline is to be understood as meaning (1S,5R)-2-azabicyclo[3.1.0]hexane-1-carboxylic acid. (2S,3R)-2,3-methano-homoproline is to be understood as meaning (1S,6R)-2-azabicyclo[4.1.0]heptane-1-carboxylic acid.

A compound having a (3α) or (3β) configuration is to be understood as being a compound selected from the (3R) and (3S) stereoisomers, it being understood that when the (3α) compound represents one of the (3R) or (3S) stereoisomers then the (3β) compound represents the other stereoisomer, the absolute configuration of the carbon atom at position 3 not being defined.

The starting materials used are known or are prepared according to known preparation procedures.

Preparations A to H result in synthesis intermediates for use in the preparation of the compounds of the invention.

The structures of the compounds described in the Examples were determined according to customary spectrophotometric techniques (infrared, NMR, mass spectrometry, . . . ).

PREPARATION A

Benzyl (2S,3R)-2,3-methano-prolinate

The expected product is obtained in accordance with the process described by A. Hercouet et al. (Tetrahedron: Asymmetry 1996, Vol. 7 No 5, pp. 1267–1268).

PREPARATION B

Benzyl (2S,3R)-2,3-methano-homoprolinate

The expected product is obtained in accordance with the process described by A. Hercouet et al. (Tet. Lett. 1996, Vol. 37 No 26, pp. 4529–4532).

PREPARATION C

Benzyl [4-Aminomethylphenyl]-(imino)-methylcarbamate

The expected product is obtained in accordance with the process described by G. De Nanteuil et al. (Synth. Comm. 1998, Vol. 28 No 23, pp. 4419–4429).

PREPARATION D

6-Amino-3-aminomethylpyridine

Lithium aluminium hydride (21 mmol) is added in small portions to 10 mmol of 6-aminonicotinamide in tetrahydrofuran. The mixture is heated at reflux for 72 hours, then brought to ambient temperature and hydrolyzed with water and then with a 1N sodium hydroxide solution. After stirring for one hour, the mixture is filtered through Celite and washed with an 85/15 tetrahydrofuran/methanol mixture. The solvents are then evaporated off and the residue obtained is purified by chromatography on silica gel to yield the expected product in the form of a white solid.

PREPARATION E

6-Amino-3-aminomethyl-2-methylpyridine

Step A: 6-Amino-3-cyano-2-methylpyridine

Copper(I) cyanide (12 mmol) is added to 10 mmol of 6-amino-3-bromo-2-methylpyridine dissolved in dimethylformamide. The mixture is heated at reflux for 10 hours and then cooled to 80° C. and poured into a solution of sodium cyanide (40 mmol) in water. After stirring for one hour at ambient temperature, the mixture is extracted with ethyl acetate. The organic phase is washed and then dried and evaporated to yield the expected product in the form of an ochre solid.

Step B: 6-Amino-3-aminomethyl-2-methylpyridine

The expected product is obtained in accordance with the process described in Step B of Example 1 starting from the compound described in the above Step and using Raney nickel as catalyst.

PREPARATION F

6-Amino-3-aminomethyl-5-methylpyridine

The expected product is obtained in accordance with the process described in Preparation E starting from 6-amino-3-bromo-5-methylpyridine.

PREPARATION G

Benzyl [4-aminomethylanilino]-(imino)-methylcarbamate

Step A: Di-(tert-butyl) 4-[(amino-(imino)-methyl)amino]benzylimidodicarbonate 10 mmol of di-(tert-butyl) 4-aminobenzylimidodicarbonate and 100 mmol of cyanamide are heated at reflux for 2 days in 80 ml of anhydrous ethanol. Removal of the ethanol by evaporation, and purification by chromatography on silica, yield the expected product.

Step B: Benzyl 4-[di-(tert-butoxycarbonyl)aminomethyl]anilino-(imino)methylcarbamate 99 mmol of 4N sodium hydroxide solution and then, at 5° C. and dropwise, 24 mmol of benzyl chloroformate, are added to 10 mmol of the compound obtained in the above Step dissolved in tetrahydrofuran. After stirring for one night at ambient temperature, the reaction mixture is decanted, the organic phase is evaporated and the residue obtained is washed with ethyl acetate, filtered and then dried to yield the expected product.

Step C: Benzyl [4-aminomethylanilino]-(imino)-methylcarbamate

A stream of HCl is passed at 0° C. for 30 minutes, with stirring, into a solution of the compound described in the above Step (10 mmol) in ethyl acetate. After stirring for one night at ambient temperature, the precipitate formed is filtered off, washed with ethyl acetate and then dried in vacuo using a dessicator.

PREPARATION H

Benzyl [4-aminomethylanilino]-carbothioyl-carbamate

The expected product is obtained in accordance with the process described in Preparation G starting from di-(tert-butyl) 4-aminobenzylimidodicarbonate and thiocyanic acid.

EXAMPLE 1

1-[(2R)-3-Cyclohexylalanyl]-N-[(6-amino-2-methyl-3-pyridyl)-methyl]-(2S,3R)-2,3-methano-prolinamide dihydrochloride

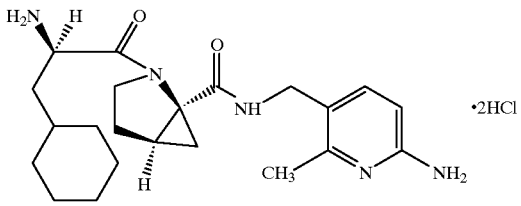

Step A: Benzyl 1-[N-tert-butoxycarbonyl-(2R)-3-cyclohexylalanyl]-(2S,3R)-2,3-methano-prolinate TBTU (11 mmol), HOBT (11 mmol) and diisopropylethylamine (22 mmol) are added to a solution in dimethylformamide of the compound described in Preparation A (10 mmol) and of N-tert-butoxycarbonyl-(2R)-3-cyclohexylalanine (10 mmol). After stirring for one night at ambient temperature, the solvent is evaporated off. The residue obtained is taken up in ethyl acetate. The organic phase is washed, and then dried and evaporated to yield the expected product in the form of an oil.

Step B: 1-[N-Tert-butoxycarbonyl-(2R)-3-cyclohexylalanyl]-(2S,3R)-2,3-methano-proline A solution of the compound described in the above Step (10 mmol) in ethanol is placed under hydrogen for one night in the presence of 10% Pd/C (0.5 g). After removal of the catalyst by filtration, the solvent is evaporated off to yield a white vitreous solid.

Step C: 1-[N-Tert-butoxycarbonyl-(2R)-3-cyclohexylalanyl]-N-[(6-amino-2-methyl-3-pyridyl)methyl]-(2S,3R)-2,3-methano-prolinamide TBTU (11 mmol) and diisopropylethylamine (11 mmol) are added to a solution in dimethylformamide of the compound described in the above Step (10 mmol) and of the compound described in Preparation E (10 mmol). After stirring for one night at ambient temperature, the solvent is evaporated off. The residue obtained is taken up in ethyl acetate. The organic phase is washed, dried and then evaporated. The expected product is obtained by purification of the residue by chromatography on silica gel using a 1/1 dichloromethane/ethyl acetate mixture as eluant.

Step D: 1-[(2R)-3-Cyclohexylalanyl]-N-[(6-amino-2-methyl-3-pyridyl)methyl]-(2S,3R)-2,3-methano-prolinamide dihydrochloride At 0° C., with stirring, a stream of HCl gas is passed into a solution of the compound described in the above Step (10 mmol) in ethyl acetate for 30 minutes. After stirring for one night at ambient temperature, the precipitate formed is filtered off, washed with ethyl acetate and then dried in vacuo using a dessicator.

Elemental Microanalysis:

|  | % C | % H | % N | % Cl |
|---|---|---|---|---|
| Calculated: | 55.93 | 7.47 | 14.82 | 15.01 |
| Found: | 55.93 | 7.68 | 14.10 | 14.47 |

Melting point: >200° C.

EXAMPLE 2

1-[(2R)-3-Cyclohexylalanyl]-N-(4-amidinobenzyl)-(2S,3R)-2,3-methano-prolinamide dihydrochloride Step A: 1-[(2R)-3-Cyclohexylalanyl]-N-[4-(benzyloxycarbonylamino-(imino)-methyl)benzyl]-(2S,3R)-2,3-methano-prolinamide dihydrochloride The expected product is obtained in accordance with the process described in Example 1 starting from the compound described in Preparation A, N-tert-butoxycarbonyl-(2R)-3-cyclohexylalanine and the compound described in Preparation C.

Step B: 1-[(2R)-3-Cyclohexylalanyl]-N-(4-amidinobenzyl)-(2S,3R)-2,3-methano-prolinamide dihydrochloride The expected product is obtained in accordance with the process described in Step B of Example 1, starting from the compound described in the above Step.

Elemental Microanalysis:

|  | % C | % H | % N | % Cl |
|---|---|---|---|---|
| Calculated: | 57.02 | 7.30 | 14.46 | 14.63 |
| Found: | 57.56 | 7.23 | 14.46 | 15.17 |

EXAMPLE 3

1-[N-Carboxymethyl-(2R)-3-cyclohexylalanyl]-N-(4-amidinobenzyl)-(2S,3R)-2,3-methano-prolinamide hydrochloride Step A: 1-[N-Benzylcarboxymethyl-(2R)-3-cyclohexylalanyl]-N-(4-amidinobenzyl)-(2S,3R)-2,3-methano-prolinamide Potassium carbonate (30 mmol) and then benzyl 2-bromoacetate (11 mmol) are added to a solution of the compound described Example 2 (10 mmol) in acetonitrile. After stirring for one night, the solution is filtered and evaporated, the residue is taken up in ethyl acetate and the organic phase is washed and dried and then evaporated.

Step B: 1-[N-Carboxymethyl-(2R)-3-cyclohexylalanyl]-N-(4-amidinobenzyl)-(2S,3R)-2,3-methano-prolinamide The expected product is obtained in accordance with the process described in Step B of Example 1, starting from the compound obtained in the above Step.

Step C: 1-[N-Carboxymethyl-(2R)-3-cyclohexylalanyl]-N-(4-amidinobenzyl)-(2S,3R)-2,3-methano-prolinamide hydrochloride The expected product is obtained in accordance with the process described in Step D of Example 1, starting from the compound obtained in the above Step.

Elemental Microanalysis

|  | % C | % H | % N | % Cl |
|---|---|---|---|---|
| Calculated: | 59.34 | 7.17 | 13.84 | 7.01 |
| Found: | 59.43 | 7.16 | 13.73 | 7.60 |

EXAMPLE 4

1-[N-Methyl-(2R)-3-cyclohexylalanyl]-N-(4-isothioureidobenzyl)-(2S,3R)-2,3-methano-prolinamide dihydrochloride Step A: 1-[(2R)-3-Cyclohexylalanyl]-N-(4-isothioureidobenzyl)-(2S,3R)-2,3-methano-prolinamide dihydrochloride The expected product is obtained in accordance with the process described in Example 2, starting from the compound described in Preparation A, N-tert-butoxycarbonyl-(2R)-3-cyclohexylalanine and the compound described in Preparation H.

Step B: 1-[N-Methyl-(2R)-3-cyclohexylalanyl]-N-(4-isothioureidobenzyl)-(2S,3R)-2,3-methano-prolinamide The expected product is obtained in accordance with the process described in J. Org. Chem. 1996, 61, 3849–3862 starting from the compound obtained in the above Step and formaldehyde, in the presence of sodium triacetoxyborohydride.

Step C: 1-[N-Methyl-(2R)-3-cyclohexylalanyl]-N-(4-isothioureidobenzyl)-(2S,3R)-2,3-methano-prolinamide dihydrochloride The expected product is obtained in accordance with the process described in Step D of Example 1, starting from the compound described in the above Step.

EXAMPLE 5

1-[N-Benzyl-(2R)-3-cyclohexylalanyl]-N-(4-isothioureidobenzyl)-(2S,3R)-2,3-methano-prolinamide dihydrochloride Step A: 1-[N-Benzyl-(2R)-3-cyclohexylalanyl]-N-(4-isothioureidobenzyl)-(2S,3R)-2,3-methano-prolinamide Diisopropylethylamine (30 mmol) and then, dropwise, benzyl chloride (11 mmol) are added to a solution at 0° C. of the compound obtained in Step A of Example 4 (10 mmol) in dichloromethane. After stirring for 4 hours at 0° C., the solution is hydrolysed and the organic phase is washed with a 1N hydrochloric acid solution and then with water and is subsequently evaporated. The expected product is obtained by purification of the residue by chromatography on silica gel using as eluant a dichloromethane/ethyl acetate mixture.

Step B: 1-[N-Benzyl-(2R)-3-cyclohexylalanyl]-N-(4-isothioureidobenzyl)-(2S,3R)-2,3-methano-prolinamide dihydrochloride The expected product is obtained in accordance with the process described in Step D of Example 1, starting from the compound described in the above Step.

EXAMPLE 6

1-[N-Methyl-(2R)-3-cyclohexylalanyl]-N-(4-guanidinobenzyl)-(2S,3R)-2,3-methano-prolinamide dihydrochloride Step A: 1-[(2R)-3-Cyclohexylalanyl]-N-(4-guanidinobenzyl)-(2S,3R)-2,3-methano-prolinamide dihydrochloride The expected product is obtained in accordance with the process described in Example 2 starting from the compound described in Preparation A, N-tert-butoxycarbonyl-(2R)-3-cyclohexylalanine and the compound described in Preparation G.

Step B: 1-[N-Methyl-(2R)-3-cyclohexylalanyl]-N-(4-guanidinobenzyl)-(2S,3R)-2,3-methano-prolinamide dihydrochloride The expected product is obtained in accordance with the process described in Steps B and C of Example 4 starting from the compound obtained in the above Step.

EXAMPLE 7

1-[N-Benzyl-(2R)-3-cyclohexylalanyl]-N-(4-guanidinobenzyl)-(2S,3R)-2,3-miethano-prolinamide dihydrochloride The expected product is obtained in accordance with the process described in Example 5 starting from the compound obtained in Step A of Example 6.

EXAMPLE 8

1-[(2R)-3-Phenylalanyl]-N-(4-amidinobenzyl)-(2S,3R)-2,3-methano-prolinamide dihydrochloride The expected product is obtained in accordance with the process described in Example 2, starting from the compound described in Preparation A, N-tert-butoxycarbonyl-(2R)-3-phenylalanine and the compound described in Preparation C.

Elemental Microanalysis:

|  | % C | % H | % N | % Cl |
|---|---|---|---|---|
| Calculated: | 57.74 | 6.11 | 14.64 | 14.82 |
| Found: | 57.64 | 5.91 | 14.45 | 14.65 |

EXAMPLE 9

1-[N-Benzylsulphonyl-(2R)-3-phenylalanyl]-N-(4-amidinobenzyl)-(2S,3R)-2,3-methano-prolinamide hydrochloride Step A: 1-[N-Benzylsulphonyl-(2R)-3-phenylalanyl]-N-(4-amidinobenzyl)-(2S,3R)-2,3-methano-prolinamide Diisopropylethylamine (30 mmol) and then, dropwise, phenylmethanesulphonyl chloride (11 mmol) are added to a solution at 0° C. of the compound described in Example 8 (10 mmol) in dichloromethane. After stirring for 4 hours at 0° C., the solution is hydrolysed, and the organic phase is washed with a 1N hydrochloric acid solution and then with water and is subsequently evaporated. The expected product is obtained by purification of the residue by chromatography on silica gel using as eluant a dichloromethane/ethyl acetate mixture.

Step B: 1-[N-Benzylsulphonyl-(2R)-3-phenylalanyl]-N-(4-amidinobenzyl)-(2S,3R)-2,3-methano-prolinamide hydrochloride The expected product is obtained in accordance with the process described in Step D of Example 1, starting from the compound described in the above Step.

Elemental Microanalyis:

|  | % C | % H | % N | % Cl | % S |
|---|---|---|---|---|---|
| Calculated: | 60.44 | 5.75 | 11.75 | 5.95 | 5.38 |
| Found: | 60.90 | 5.67 | 11.50 | 6.11 | 5.11 |

EXAMPLE 10

1-[N-Carboxymethyl-(2R)-3-phenylalanyl]-N-(4-amidinobenzyl)-(2S,3R)-2,3-methano-prolinamide hydrochloride The expected product is obtained in accordance with the process described in Example 3, starting from the compound described in Example 8.
Elemental Microanalysis

|  | % C | % H | % N | % Cl |
|---|---|---|---|---|
| Calculated: | 57.13 | 5.90 | 13.33 | 11.47 |
| Found: | 57.65 | 5.51 | 13.40 | 11.51 |

EXAMPLE 11

1-[(2R)-3,3-Diphenylalanyl]-N-(4-amidinobenzyl)-(2S,3R)-2,3-methano-prolinamide dihydrochloride The expected product is obtained in accordance with the process described in Example 2, starting from the compound described in Preparation A, N-tert-butoxycarbonyl-(2R)-3,3-diphenylalanine and the compound described in Preparation C.
Elemental Microanalysis:

|  | % C | % H | % N | % Cl |
|---|---|---|---|---|
| Calculated: | 62.81 | 6.00 | 12.63 | 12.79 |
| Found: | 63.12 | 6.02 | 12.71 | 13.22 |

EXAMPLE 12

1-[(2R)-3,3-Diphenylalanyl]-N-[(6-amino-3-pyridyl)methyl]-(2S,3R)-2,3-methano-prolinamide dihydrochloride The expected product is obtained in accordance with the process described in Example 1, starting from the compound described in Preparation A, N-tert-butoxycarbonyl-(2R)-3,3-diphenylalanine and the compound described in Preparation D.
Elemental Microanalysis:

|  | % C | % H | % N | % Cl |
|---|---|---|---|---|
| Calculated: | 61.36 | 5.91 | 13.25 | 13.42 |
| Found: | 61.98 | 6.04 | 13.46 | 13.67 |

EXAMPLE 13

1-[(2R)-3,3-Dicyclohexylalanyl]-N-(4-amidinobenzyl)-(2S,3R)-2,3-methano-prolinamide dihydrochloride
Step A: N-Tert-butoxycarbonyl-(2R)-3,3-dicyclohexylalanine A solution of N-tert-butoxycarbonyl-(2R)-3,3-diphenylalanine (10 mmol) in ethanol is placed under hydrogen for one night in the presence of Rh/C (0.5 g). After removal of the catalyst by filtration, the solvent is evaporated off to yield the expected product.
Step B: 1-[(2R)-3,3-Dicyclohexylalanyl]-N-(4-amidinobenzyl)-(2S,3R)-2,3-methano-prolinamide dihydrochloride The expected product is obtained in accordance with the process described in Example 2, starting from the compound described in Preparation A, the compound described in the above Step and the compound described in Preparation C.
Elemental Microanalysis:

|  | % C | % H | % N | % Cl |
|---|---|---|---|---|
| Calculated: | 61.47 | 8.00 | 12.36 | 12.51 |
| Found: | 61.88 | 7.89 | 12.32 | 12.46 |

EXAMPLE 14

1-[N-Carboxymethyl-(2R)-3,3-dicyclohexylalanyl]-N-(4-amidinobenzyl)-(2S,3R)-2,3-methano-prolinamide hydrochloride The expected product is obtained in accordance with the process described in Example 3, starting from the compound described in Example 13.
Elemental Microanalysis

|  | % C | % H | % N | % Cl |
|---|---|---|---|---|
| Calculated: | 63.30 | 7.88 | 11.91 | 6.03 |
| Found: | 63.78 | 7.50 | 11.81 | 6.21 |

EXAMPLE 15

1-[(2R)-Cyclohexylglycyl]-N-(4-amidinobenzyl)-(2S,3R)-2,3-methano-prolinamide dihydrochloride The expected product is obtained in accordance with the process described in Example 2, starting from the compound described in Preparation A, N-tert-butoxycarbonyl-(2R)-cyclohexylglycine and the compound described in Preparation C.

EXAMPLE 16

1-[N-Benzylsulphonyl-(2R)-cyclohexylglycyl]-N-(4-amidinobenzyl)-(2S,3R)-2,3-methano-prolinamide hydrochloride The expected product is obtained in accordance with the process described in Example 9, starting from the compound described in Example 15.
Elemental Microanalysis

|  | % C | % H | % N | % Cl | % S |
|---|---|---|---|---|---|
| Calculated: | 59.22 | 6.51 | 11.91 | 6.03 | 5.45 |
| Found: | 59.31 | 637 | 11.93 | 6.49 | 5.26 |

EXAMPLE 17

1-[N-Carboxymethyl-(2R)-cyclohexylglycyl]-N-(4-amidinobenzyl)-(2S,3R)-2,3-methano-prolinamide hydrochloride The expected product is obtained in accordance with the process described in Example 3, starting from the compound described in Example 15.

Elemental Microanalysis:

|  | % C | % H | % N | % Cl |
|---|---|---|---|---|
| Calculated: | 58.59 | 6.96 | 14.23 | 7.51 |
| Found: | 59.15 | 6.53 | 14.14 | 8.48 |

EXAMPLE 18

1-[N-Ethoxycarbonylmethyl-(2R)-cyclohexylglycyl]-N-(4-amidinobenzyl)-(2S,3R)-2,3-methano-prolinamide dihydrochloride The expected product is obtained in accordance with the process described in Example 9, starting from ethyl bromoacetate and the compound described in Example 15.
Elemental Microanalysis:

|  | % C | % H | % N | % Cl |
|---|---|---|---|---|
| Calculated: | 56.11 | 7.06 | 12.58 | 12.74 |
| Found: | 56.92 | 7.18 | 12.81 | 12.78 |

EXAMPLE 19

1-[N-Carboxymethyl-(2R)-leucyl]-N-(4-amidinobenzyl)-(2S,3R)-2,3-methano-prolinamide hydrochloride Step A: 1-[(2R)-Leucyl]-N-(4-amidinobenzyl)-(2S,3R)-2,3-methano-prolinamide dihydrochloride The expected product is obtained in accordance with the process described in Example 2 starting from the compound described in Preparation A, N-tert-butoxycarbonyl-(2R)-leucine and the compound described in Preparation C.

Step B: 1-[N-Carboxymethyl-(2R)-leucyl]-N-(4-amidinobenzyl)-(2S,3R)-2,3-methano-prolinamide dihydrochloride The expected product is obtained in accordance with the process described in Example 3 starting from the compound described in the above Step.
Elemental Microanalysis:

|  | % C | % H | % N | % Cl |
|---|---|---|---|---|
| Calculated: | 56.71 | 6.92 | 15.03 | 7.61 |
| Found: | 56.63 | 7.02 | 14.81 | 8.20 |

EXAMPLE 20

1-[N-Methyl-(2R)-phenylglycyl]-N-(4-amidinobenzyl)-(2S,3R)-2,3-methano-prolinamide dihydrochloride Step A: 1-[(2R)-2-Phenylglycyl]-N-(4-amidinobenzyl)-(2S,3R)-2,3-methano-prolinamide dihydrochloride The expected product is obtained in accordance with the process described in Example 2 starting from the compound described in Preparation A, N-tert-butoxycarbonyl-(2R)-phenylglycine and the compound described in Preparation C.

Step B: 1-[N-Methyl-(2R)-phenylglycyl]-N-(4-amidinobenzyl)-(2S,3R)-2,3-methano-prolinamide dihydrochloride The expected product is obtained in accordance with the process described in Steps B and C of Example 4 starting from the compound described in the above Step.

EXAMPLE 21

1-[N-Benzyl-(2R)-phenylglycyl]-N-(4-amidinobenzyl)-(2S,3R)-2,3-methano-prolinamide dihydrochloride The expected product is obtained in accordance with the process described in Example 5, starting from the compound described in Step A of Example 20.

EXAMPLE 22

1-[(2R)-3-Cyclohexyl-2-hydroxypropionyll-N-(4-amidinobenzyl)-(2S,3R)-2,3-methano-prolinamide hydrochloride Step A: (2R)-3-Cyclohexyl-2-hydroxypropionic Acid The expected product is obtained in accordance with the process described in Step A of Example 13 starting from (2R)-2-hydroxy-3-phenylpropionic acid.

Step B: (2R)-2-Acetoxy-3-cyclohexylpropionic Acid

Acetic anhydride (11 mmol) is added to 10 mmol of the compound obtained in the above Step dissolved in pyridine. After stirring for one hour at ambient temperature, the reaction mixture is poured into water and methyl tert-butyl ether is added. The organic phase is washed, dried and then evaporated to yield the expected product.

Step C: 1-[(2R)-2-Acetoxy-3-cyclohexylpropionyl]-N-[4-(benzyloxy-carbonylamino-(imino)-methyl)benzyl]-(2S,3R)-2,3-methano-prolinamide The expected product is obtained in accordance with the process described in Steps A to C of Example 1, starting from the compound described in Preparation A, the compound described in the above Step and the compound described in Preparation C.

Step D: 1-[(2R)-3-Cyclohexyl-2-hydroxypropionyl]-N-[4-(benzyloxy-carbonylamino-(imino)-methyl)benzyl]-(2S,3R)-2,3-methano-prolinamide A 1N sodium hydroxide solution is added to 10 mmol of the compound described in the above Step dissolved in tetrahydrofuran. After stirring for one hour at ambient temperature, ethyl acetate is added and the organic phase is washed, dried and then evaporated to yield the expected product.

Step E: 1-[(2R)-3-Cyclohexyl-2-hydroxypropionyl]-N-(4-amidinobenzyl)-(2S,3R)-2,3-methano-prolinamide hydrochloride A solution of the compound described in the above Step (10 mmol) in 1N hydrochloric acid in ethanol is placed under hydrogen for one night in the presence of 10% Pd/C (0.5 g). After removal of the catalyst by filtration, the solvent is evaporated off to yield the expected product.
Elemental Microanalysis:

|  | % C | % H | % N | % Cl |
|---|---|---|---|---|
| Calculated: | 61.53 | 7.41 | 12.48 | 7.90 |
| Found: | 61.36 | 7.40 | 12.45 | 8.47 |

EXAMPLE 23

1-[(2R)-3-Cyclohexylalanyl]-N-(4-amidinobenzyl)-(2S,3R)-2,3-methano-homoprolinamide dihydrochloride The expected product is obtained in accordance with the process described in Example 2, starting from the compound described in Preparation B, N-tert-butoxycarbonyl-(2R)-3-cyclohexylalanine and the compound described in Preparation C.

EXAMPLE 24

1-[N-Carboxymethyl-(2R)-3-cyclohexylalanyl]-N-(4-amidinobenzyl)-(2S,3R)-2,3-methano-homoprolinamide hydrochloride The expected product is obtained in accordance with the process described in Example 3, starting from the compound described in Example 23.

Elemental Microanalysis:

|  | % C | % H | % N | % Cl |
|---|---|---|---|---|
| Calculated: | 60.05 | 7.36 | 13.47 | 6.82 |
| Found: | 59.52 | 7.18 | 12.70 | 7.67 |

EXAMPLE 25

1-[N-Ethoxycarbonylmethyl-(2R)-3-cyclohexylalanyl]-N-(4-amidinobenzyl)-(2S,3R)-2,3-methano-homoprolinamide dihydrochloride The expected product is obtained in accordance with the process described in Example 9, starting from ethyl bromoacetate and the compound described in Example 23.

Elemental Microanalysis:

|  | % C | % H | % N | % Cl |
|---|---|---|---|---|
| Calculated: | 57.53 | 7.41 | 11.98 | 12.13 |
| Found: | 58.29 | 7.43 | 11.89 | 11.75 |

EXAMPLE 26

1-[N-Carbamoylmethyl-(2R)-3-cyclohexylalanyl]-N-(4-amidino-benzyl)-(2S,3R)-2,3-methano-homoprolinamide dihydrochloride The expected product is obtained in accordance with the process described in Example 9, starting from 2-bromoacetamide and the compound described in Example 23.

EXAMPLE 27

1-[(2R)-3-Cyclohexylalanyl]-N-[(6-amino-3-pyridyl)methyl]-(2S,3R)-2,3-methano-homoprolinamide dihydrochloride The expected product is obtained in accordance with the process described in Example 1, starting from the compound described in Preparation B, N-tert-butoxycarbonyl-(2R)-3-cyclohexylalanine and the compound described in Preparation D.

Elemental Microanalysis:

|  | % C | % H | % N | % Cl |
|---|---|---|---|---|
| Calculated: | 55.93 | 7.47 | 14.82 | 15.01 |
| Found: | 55.91 | 7.38 | 14.67 | 15.33 |

EXAMPLE 28

1-[(2R)-3-Cyclohexylalanyl]-N-[(6-amino-2-methyl-3-pyridyl)methyl]-(2S,3R)-2,3-methano-homoprolinamide dihydrochloride The expected product is obtained in accordance with the process described in Example 1, starting from the compound described in Preparation B, N-tert-butoxycarbonyl-(2R)-3-cyclohexylalanine and the compound described in Preparation E.

Elemental Microanalysis:

|  | % C | % H | % N | % Cl |
|---|---|---|---|---|
| Calculated: | 56.79 | 7.67 | 14.40 | 14.57 |
| Found: | 57.37 | 7.87 | 14.21 | 14.82 |

EXAMPLE 29

1-[N-Methyl-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Steps B and C of Example 4, starting from the compound described in Example 28.

Elemental Microanalysis:

|  | % C | % H | % N | % Cl |
|---|---|---|---|---|
| Calculated: | 57.59 | 7.85 | 13.99 | 14.17 |
| Found: | 57.63 | 7.53 | 13.95 | 14.66 |

EXAMPLE 30

1-[N-Ethyl-(2R)-3-cyclohexylalanyl]-N-1(6-amino-2-methyl-3-pyridyl)methyl]-(2S,3R)-2,3-methano-homoprolinamide dihydrochloride Step A: 1-[N-Ethyl-(2R)-3-cyclohexylalanyl]-N-[(6-amino-2-methyl-3-pyridyl)methyl]-(2S,3R)-2,3-methano-homoprolinamide The expected product is obtained in accordance with the process described in J. Org. Chem., 1996, 61, 3849–3862 starting from the compound described in Example 28 and acetaldehyde, in the presence of sodium triacetoxyborohydride.

Step B: 1-[N-Ethyl-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Step D of Example 1 starting from the compound described in the above Step.

EXAMPLE 31

1-[N-Butyl-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 30 starting from the compound described in Example 28 and butyraldehyde.

Elemental Microanalysis:

|  | % C | % H | % N | % Cl |
|---|---|---|---|---|
| Calculated: | 59.77 | 8.36 | 12.91 | 13.07 |
| Found: | 60.14 | 8.25 | 12.83 | 13.29 |

EXAMPLE 32

1-[N-Carboxymethyl-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 3, starting from the compound described in Example 28.
Elemental Microanalysis:

|  | % C | % H | % N | % Cl |
|---|---|---|---|---|
| Calculated: | 55.14 | 7.23 | 12.86 | 13.02 |
| Found: | 55.73 | 7.24 | 12.68 | 13.00 |

EXAMPLE 33

1-[N-Ethoxycarbonylmethyl-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 9, starting from ethyl bromoacetate and the compound described in Example 28.
Elemental Microanalysis:

|  | % C | % H | % N | % Cl |
|---|---|---|---|---|
| Calculated: | 56.64 | 7.57 | 12.07 | 12.35 |
| Found: | 56.55 | 7.58 | 12.23 | 12.38 |

EXAMPLE 34

1-[N-Ethoxycarbonylmethoxycarbonylmethyl-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 9, starting from ethyl bromoacetate and the compound described in Example 32.
Elemental Microanalysis:

|  | % C | % H | % N | % Cl |
|---|---|---|---|---|
| Calculated: | 55.24 | 7.19 | 11.11 | 11.24 |
| Found: | 55.60 | 7.23 | 11.29 | 11.34 |

EXAMPLE 35

1-[N-(Carbamoylmethyl)-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 9, starting from 2-bromoacetamide and the compound described in Example 28.

Elemental Microanalysis:

|  | % C | % H | % N | % Cl |
|---|---|---|---|---|
| Calculated: | 55.24 | 7.42 | 15.46 | 13.05 |
| Found: | 55.66 | 7.25 | 15.41 | 12.98 |

EXAMPLE 36

1-[N-Benzyl-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 5, starting from the compound described in Example 28.
Elemental Microanalysis:

|  | % C | % H | % N | % Cl |
|---|---|---|---|---|
| Calculated: | 62.49 | 7.52 | 12.15 | 12.30 |
| Found: | 62.38 | 7.64 | 11.47 | 11.52 |

EXAMPLE 37

1-[N-(4-Hydroxybenzyl)-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 30 starting from the compound described in Example 28 and 4-acetoxybenzaldehyde.
Elemental Microanalysis:

|  | % C | % H | % N | % Cl |
|---|---|---|---|---|
| Calculated: | 60.80 | 7.31 | 11.82 | 11.96 |
| Found: | 60.20 | 7.59 | 11.35 | 11.61 |

EXAMPLE 38

1-[N-(4-Carboxybenzyl)-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 30 starting from the compound described in Example 28 and 4-(methoxycarbonyl)-benzaldehyde.
Elemental Microanalysis:

|  | % C | % H | % N | % Cl |
|---|---|---|---|---|
| Calculated: | 60.00 | 6.98 | 11.28 | 11.43 |
| Found: | 60.55 | 7.14 | 11.37 | 11.12 |

EXAMPLE 39

1-[N-(3,4-Dimethoxybenzyl)-(2R)-3-cyclohexylaianyl]-N-[(6-amino-2-methyl-3-pyridyl)methyl]-(2S,3R)-2,3-methano-homoprolinamide dihydrochloride The expected product is obtained in accordance with the process described in Example 30 starting from the compound described in Example 28 and (3,4-dimethoxy)benzaldehyde.

Elemental Microanalysis:

|  | % C | % H | % N | % Cl |
|---|---|---|---|---|
| Calculated: | 60.37 | 7.44 | 10.67 | 10.73 |
| Found: | 60.49 | 7.47 | 11.00 | 11.14 |

EXAMPLE 40

1-[N-[(Biphenylyl)methyl]-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 30 starting from the compound described in Example 28 and 4-biphenylcarbaldehyde.

Elemental Microanalysis:

|  | % C | % H | % N | % Cl |
|---|---|---|---|---|
| Calculated: | 66.25 | 7.26 | 10.73 | 10.86 |
| Found: | 66.65 | 7.17 | 10.75 | 11.10 |

EXAMPLE 41

1-[N-[(2-Naphthyl)methyl]-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 30 starting from the compound described in Example 28 and 2-naphthalenecarbaldehyde.

Elemental Microanalysis:

|  | % C | % H | % N | % Cl |
|---|---|---|---|---|
| Calculated: | 65.17 | 7.24 | 11.18 | 11.31 |
| Found: | 65.49 | 7.42 | 10.84 | 10.64 |

EXAMPLE 42

1-[N-Phenethyl-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 30 starting from the compound described in Example 28 and phenyl acetaldehyde.

Elemental Microanalysis:

|  | % C | % H | % N | % Cl |
|---|---|---|---|---|
| Calculated: | 63.04 | 7.68 | 11.86 | 12.00 |
| Found: | 63.28 | 7.62 | 11.73 | 12.01 |

EXAMPLE 43

1-[N-[(4-Pyridyl)methyl]-(2R)-3-cyclohexylalanyl]-N-[(6-amino-2-methyl-3-pyridyl)methyl]-(2S,3R)-2,3-methano-homoprolinamide trihydrochloride The expected product is obtained in accordance with the process described in Example 30 starting from the compound described in Example 28 and isonicotinaldehyde.

Elemental Microanalysis:

|  | % C | % H | % N | % Cl |
|---|---|---|---|---|
| Calculated: | 56.72 | 7.06 | 13.69 | 17.32 |
| Found: | 56.30 | 7.14 | 13.37 | 18.10 |

EXAMPLE 44

1-[N-[(2-Pyridyl)methyl]-(2R)-3-cyclohexylalanyl]-N-[(6-amino-2-methyl-3-pyridyl)methyl]-(2S,3R)-2,3-mnethano-homoprolinamide dihydrochloride The expected product is obtained in accordance with the process described in Example 30 starting from the compound described in Example 28 and 2-pyridinecarbaldehyde.

Elemental Microanalysis:

|  | % C | % H | % N | % Cl |
|---|---|---|---|---|
| Calculated: | 60.31 | 7.33 | 14.55 | 12.28 |
| Found: | 60.70 | 7.33 | 14.52 | 12.85 |

EXAMPLE 45

1-[N-[(4-Quinolyl)methyl]-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 30 starting from the compound described in Example 28 and 4-quinolinecarbaldehyde.

Elemental Microanalysis:

|  | % C | % H | % N | % Cl |
|---|---|---|---|---|
| Calculated: | 63.14 | 7.08 | 13.39 | 11.30 |
| Found: | 63.38 | 6.93 | 13.40 | 11.79 |

EXAMPLE 46

1-[N-[(2-Quinolyl)methyl]-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 30 starting from the compound described in Example 28 and 2-quinolinecarbaldehyde.

Elemental Microanalysis:

|  | % C | % H | % N | % Cl |
|---|---|---|---|---|
| Calculated: | 63.14 | 7.08 | 13.39 | 11.30 |
| Found: | 62.70 | 7.14 | 13.53 | 11.67 |

EXAMPLE 47

1-[N-[(4,5-Dihydro-1H-2-imidazolyl)methyl]-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 9 starting from the compound described in Example 28 and 2-(chloromethyl)-4,5-dihydro-1H-imidazole.

Elemental Microanalysis:

|  | % C | % H | % N | % Cl |
|---|---|---|---|---|
| Calculated: | 57.04 | 7.62 | 17.24 | 12.47 |
| Found: | 57.88 | 7.56 | 17.19 | 12.64 |

EXAMPLE 48

1-[N-Propargyl-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 9, starting from propargyl bromide and the compound described in Example 28.

EXAMPLE 49

1-[N-((4-Morpholinyl)ethyl)-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 9, starting from 4-(2-chloroethyl)-morpholine and the compound described in Example 28.

EXAMPLE 50

1-[N-((2-Morpholinyl)methyl)-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 9, starting from 2-p-toluenesulphonyloxymethyl-morpholine and the compound described in Example 28.

EXAMPLE 51

1-[N-((4-Morpholinyl)carbonyl)-(2R)-3-cyclohexylalanyl]-N-[(6-amino-2-methyl-3-pyridyl)methyl]-(2S,3R)-2,3-methano-homoprolinamide hydrochloride The expected product is obtained in accordance with the process described in Example 9, starting from 4-morpholine-carbonyl chloride and the compound described in Example 28.

EXAMPLE 52

1-[N-Methylsulphonyl-(2R)-3-cyclohexylalanyl]-N-[(6-amino-2-methyl-3-pyridyl)methyl]-(2S,3R)-2,3-methano-homoprolinamide hydrochloride The expected product is obtained in accordance with the process described in Example 9 starting from the compound described in Example 28 and methanesulphonyl chloride.

EXAMPLE 53

1-[N-Benzylsulphonyl-(2R)-3-cyclohexylalanyl]-N-[(6-amino-2-methyl-3-pyridyl)methyl]-(2S,3R)-2,3-methano-homoprolinamide hydrochloride The expected product is obtained in accordance with the process described in Example 9 starting from the compound described in Example 28.

EXAMPLE 54

1-[N-Aminosulphonylmethyl-(2R)-3-cyclohexylalanyl]-N-[(6-amino-2-methyl-3-pyridyl)methyl]-(2S,3R)-2,3-methano-homoprolinamide dihydrochloride The expected product is obtained in accordance with the process described in Example 9, starting from the compound described in Example 28 and aminosulphonylmethyl bromide.

EXAMPLE 55

1-[(2R)-3-Cyclohexylalanyl]-N-[(6-amino-5-methyl-3-pyridyl)methyl]-(2S,3R)-2,3-methano-homoprolinamide dihydrochloride The expected product is obtained in accordance with the process described in Example 1, starting from the compound described in Preparation B, N-tert-butoxycarbonyl-(2R)-3-cyclohexylalanine and the compound described in Preparation F.

Elemental Microanalysis:

|  | % C | % H | % N | % Cl |
|---|---|---|---|---|
| Calculated: | 56.79 | 7.67 | 14.40 | 14.58 |
| Found: | 57.26 | 7.71 | 14.28 | 15.08 |

EXAMPLE 56

1-[N-Methyl-(2R)-3-cyclohexylalanyl]-N-(4-isothioureidobenzyl)-(2S,3R)-2,3-methano-homoprolinamide dihydrochloride The expected product is obtained in accordance with the process described in Example 4 starting from the compound described in Preparation B, N-tert-butoxycarbonyl-(2R)-3-cyclohexylalanine and the compound described in Preparation H.

EXAMPLE 57

1-[N-Benzyl-(2R)-3-cyclohexylalanyl]-N-(4-isothioureidobenzyl)-(2S,3R)-2,3-methano-homoprolinamide dihydrochloride The expected product is obtained in accordance with the process described in Example 5 starting from the compound described in Preparation B, N-tert-butoxycarbonyl-(2R)-3-cyclohexylalanine and the compound described in Preparation H.

EXAMPLE 58

1-[N-Methyl-(2R)-3-cyclohexylalanyl]-N-(4-guanidinobenzyl)-(2S,3R)-2,3-methano-homoprolinamide dihydrochloride The expected product is obtained in accordance with the process described in Example 4 starting from the compound described in Preparation B, N-tert-butoxycarbonyl-(2R)-3-cyclohexylalanine and the compound described in Preparation G.

EXAMPLE 59

1-[N-Benzyl-(2R)-3-cyclohexylalanyl]-N-(4-guanidinobenzyl)-(2S,3R)-2,3-methano-homoprolinamide dihydrochloride The expected product is obtained in accordance with the process described in Example 5 starting from the compound described in Preparation B, N-tert-butoxycarbonyl-(2R)-3-cyclohexylalanine and the compound described in Preparation G.

EXAMPLE 60

1-[(2R)-3-Phenylalanyl]-N-[(6-amino-2-methyl-3-pyridyl)methyl]-(2S,3R)-2,3-methano-homoprolinamide dihydrochloride The expected product is obtained in accordance with the process described in Example 1, starting from the compound described in Preparation B, N-tert-butoxycarbonyl-(2R)-3-phenylalanine and the compound described in Preparation E.
Elemental Microanalysis:

|  | % C | % H | % N | % Cl |
| --- | --- | --- | --- | --- |
| Calculated: | 57.50 | 6.50 | 14.58 | 14.76 |
| Found: | 57.52 | 6.44 | 14.21 | 14.98 |

EXAMPLE 61

1-[(2R)-3,3-Diphenylalanyl]-N-(4-amidinobenzyl)-(2S,3R)-2,3-methano-homoprolinamide dihydrochloride The expected product is obtained in accordance with the process described in Example 2, starting from the compound described in Preparation B, N-tert-butoxycarbonyl-(2R)-3,3-diphenylalanine and the compound described in Preparation C.
Elemental Microanalysis:

|  | % C | % H | % N | % Cl |
| --- | --- | --- | --- | --- |
| Calculated: | 63.38 | 6.20 | 12.32 | 12.47 |
| Found: | 63.55 | 6.17 | 12.39 | 12.56 |

EXAMPLE 62

1-[(2R)-3,3-Diphenylalanyl]-N-[(6-amino-3-pyridyl)methyl]-(2S,3R)-2,3-methano-homoprolinamide dihydrochloride The expected product is obtained in accordance with the process described in Example 1, starting from the compound described in Preparation B, N-tert-butoxycarbonyl-(2R)-3,3-diphenylalanine and the compound described in Preparation D.
Elemental Microanalysis:

|  | % C | % H | % N | % Cl |
| --- | --- | --- | --- | --- |
| Calculated: | 61.99 | 6.13 | 12.91 | 13.07 |
| Found: | 62.37 | 6.18 | 12.99 | 12.82 |

EXAMPLE 63

1-[(2R)-3,3-Dicyclohexylalanyl]-N-[(6-amino-2-methyl-3-pyridyl) methyl]-(2S,3R)-2,3-methano-homoprolinamide dihydrochloride The expected product is obtained in accordance with the process described in Example 1, starting from the compound described in Preparation B, N-tert-butoxycarbonyl-(2R)-3,3-dicyclohexylalanine and the compound described in Preparation E.
Elemental Microanalysis:

|  | % C | % H | % N | % Cl |
| --- | --- | --- | --- | --- |
| Calculated: | 61.26 | 8.33 | 12.32 | 12.47 |
| Found: | 61.03 | 8.21 | 12.48 | 12.77 |

EXAMPLE 64

1-[(2R)-3,3-Dicyclohexylalanyl]-N-[6-amino-3-pyridyl)methyl]-(2S,3R)-2,3-methano-homoprolinamide dihydrochloride The expected product is obtained in accordance with the process described in Example 2, starting from the compound described in Preparation B, N-tert-butoxycarbonyl-(2R)-3,3-dicyclohexylalanine and the compound described in Preparation D.
Elemental Microanalysis:

|  | % C | % H | % N | % Cl |
| --- | --- | --- | --- | --- |
| Calculated: | 60.64 | 8.18 | 12.63 | 12.78 |
| Found: | 60.88 | 8.10 | 12.42 | 12.86 |

EXAMPLE 65

1-[(2R)-Cyclohexylglycyl]-N-(4-amidinobenzyl)-(2S,3R)-2,3-methano-homoprolinamide dihydrochloride The expected product is obtained in accordance with the process described in Example 2, starting from the compound described in Preparation B, N-tert-butoxycarbonyl-(2R)-cyclohexylglycine and the compound described in Preparation C.

EXAMPLE 66

1-[N-Carboxymethyl-(2R)-cyclohexylglycyl]-N-(4-amidinobenzyl)-(2S,3R)-2,3-methano-homoprolinamide hydrochloride The expected product is obtained in accordance with the process described in Example 3, starting from the compound described in Example 65.

Elemental Microanalysis:

|  | % C | % H | % N | % Cl |
|---|---|---|---|---|
| Calculated: | 59.34 | 7.17 | 13.84 | 7.01 |
| Found: | 59.92 | 7.26 | 13.88 | 7.63 |

EXAMPLE 67

1-[(2R)-Cyclohexylglycyl]-N-[(6-amino-2-methyl-3-pyridyl)methyl]-(2S,3R)-2,3-methano-homoprolinamide dihydrochloride The expected product is obtained in accordance with the process described in Example 1, starting from the compound described in Preparation B, N-tert-butoxycarbonyl-(2R)-cyclohexylglycine and the compound described in Preparation E.

Elemental Microanalysis:

|  | % C | % H | % N | % Cl |
|---|---|---|---|---|
| Calculated: | 55.93 | 7.47 | 14.82 | 15.01 |
| Found: | 56.51 | 7.52 | 14.83 | 15.20 |

EXAMPLE 68

1-[(2R)-Cyclohexylglycyl]-N-[(6-amino-3-pyridyl)methyl]-(2S,3R)-2,3-methano-homoprolinamide dihydrochloride The expected product is obtained in accordance with the process described in Example 1 starting from the compound described in Preparation B, N-tert-butoxycarbonyl-(2R)-cyclohexylglycine and the compound described in Preparation D.

Elemental Microanalysis:

|  | % C | % H | % N | % Cl |
|---|---|---|---|---|
| Calculated: | 55.02 | 7.26 | 15.28 | 15.47 |
| Found: | 55.50 | 7.36 | 15.41 | 15.91 |

EXAMPLE 69

1-[(2R,3α)-3-Cyclohexyl-3-trifluoromethylalanyl]-N-(4-amidino-benzyl)-(2S,3R)-2,3-methano-homoprolinamide dihydrochloride Step A: Benzyl 3-cyclohexyl-4,4,4-tripluoro-2-butenoate 10 mmol of benzyl trimethoxyphosphonoacetate are added dropwise, at 0° C., to 10 mmol of sodium hydride suspended in 10 ml of dimethoxyethane. After stirring the mixture for one hour at ambient temperature, 10 mmol of cyclohexyl trifluoromethyl ketone are added. The reaction mixture is stirred for 1 hour at ambient temperature, and then poured into 20 ml of water. The aqueous phase is extracted with ether. The organic phase is washed, dried and then evaporated. An oil is obtained, which is distilled in vacuo at 100–110° C.

Step B: (±)-Cyclohexyl-3-trifluoromethyl-1-propionic Acid

The expected product is obtained in accordance with the process described in Step B of Example 1 starting from the compound obtained in the above Step.

Step C: (±)-3-Cyclohexyl-3-trifluoromethyl-1-propionic Acid chloride 10 mmol of thionyl choride are added at 0° C. to 10 mmol of the acid obtained in the above Step dissolved in dichloromethane. After returning to ambient temperature and stirring for one night, the solution is evaporated to yield the expected product.

Step D: (4R)-3-[3-Cyclohexyl-4,4,4-trifluoro-1-oxobutyl]-4-benzyl-2-oxazolidinone A 2.5 M n-butyllithium solution in hexane (4.2 ml) is added to a solution of (4R)-(4-benzyl)-2-oxazolidinone (10 mmol) in tetrahydrofuran. After stirring the mixture for one hour at −78° C., a solution in tetrahydrofuran of the compound obtained in the above Step (10 mmol) is added. The reaction mixture is brought to 0° C. and then poured into an aqueous ammonium chloride solution. The aqueous phase is extracted with ethyl acetate and then the combined organic phases are washed, dried and subsequently evaporated to yield the expected product in the form of a mixture of two diastereoisomers.

Step E: (4R)-3-[(3α)-3-Cyclohexyl-4,4,4-trifluoro-1-oxobutyl]-4-benzyl-2-oxazolidinone After separation of the diastereoisomers from the mixture obtained in the above Step by chromatography on silica gel using a 40/60 n-heptane/toluene mixture as eluant, the expected product is obtained by evaporation of the first of the two fractions eluted.

Step F: (4R)-3-[(2R,3α)-2-Azido-4,4,4-trifluoro-1-oxobutyl]-4-benzyl-2-oxazolidinone To a solution at −78° C. of the compound described in the above Step (10 mmol) in tetra-hydrofuran there are added dropwise a 0.5M potassium hexamethyldisilazide solution in toluene (10.5 mmol) and then, after stirring for one hour, a solution of trityl azide (11 mmol) in tetrahydrofuran. After stirring for 5 minutes, glacial acetic acid (3.5 ml) is added, and then the reaction mixture is stirred at ambient temperature for 6 hours. A solution of ammonium chloride is added and then, after extraction, the organic phase is washed, dried and evaporated to yield the expected product.

Step G: (2R,3α)-2-Azido-3-cyclohexyl-3-trifluoromethyl-1-propionic Acid

An aqueous solution of lithium hydroxide (12 mmol) and a 30% solution of hydrogen peroxide (5.7 ml) are added to a solution at 0° C. of the compound obtained in the above Step (10 mmol) in dioxane. After stirring the mixture for ½ hour at 0° C., ethyl acetate is added, and the organic phase is washed, dried and then evaporated to yield the expected product.

Step H: (2R,3α)-3-Cyclohexyl-3-trifluoromethylalanine

The expected product is obtained in accordance with the process described in Step B of Example 1 starting from the compound obtained in the above Step.

Step I: N-Tert-butoxycarbonyl-(2R,3α)-3-cyclohexyl-3-trifluoromethylalanine

A solution of 1N sodium hydroxide (11 mmol) and di-tert-butyl dicarbonate (11 mmol) are added to 10 mmol of the compound described in the above Step dissolved in tert-butanol. After stirring for one hour, the solvents are evaporated off, the residue is taken up in ethyl acetate, and the organic phase is washed, dried and evaporated to yield the expected product.

Step J: 1-[N-Tert-butoxycarbonyl-(2R,3α)-3-cyclohexyl-3-trifluoromethylalanyl]-(2S,3R)-2,3-methano-homoproline The expected product is obtained in accordance with the process described in Steps A and B of Example 1 starting from the compound described in the above Step and the compound described in Preparation B.

Step K: 1-[(2R,3α)-3-Cyclohexyl-3-trifluoromethylalanyl]-N-(4-amidino-benzyl)-(2S,3R)-2,3-methano-homoprolinamide dihydrochloride The expected product is obtained in accordance with the process described in Example 2, starting from the compound obtained in the above Step and the compound described in Preparation C.

EXAMPLE 70

1-[(2R,3β)-3-Cyclohexyl-3-trifluoromethylalanyl]-N-(4-amidino-benzyl)-(2S,3R)-2,3-methano-homoprolinamide dihydrochloride Step A: (4R)-3-[(3β)-3-Cyclohexyl-4,4,4-trifluoro-]-oxobutyl]-4-benzyl-2-oxazolidinone After separation of the diastereoisomers from the mixture described in Step D of Example 69 by chromatography on silica gel using a 40/60 n-heptane/toluene mixture as eluant, the expected product is obtained by evaporation of the second of the 2 fractions eluted.

Step B: 1-[N-Tert-butoxycarbonyl-(2R,3β)-3-cyclohexyl-3-trifluoromethylalanyl]-(2S,3R)-2,3-methano-homoproline The expected product is obtained in accordance with the process described in Steps F to J of Example 69, starting from the compound described in the above Step.

Step C: 1-[(2R,3β)-3-Cyclohexyl-3-trifluoromethylalanyl]-N-(4-amidino-benzyl)-(2S,3R)-2,3-methano-homoprolinamide dihydrochloride The expected product is obtained in accordance with the process described in Example 2, starting from the compound obtained in the above Step and the compound described in Preparation C.

EXAMPLE 71

1-[N-Carboxymethyl-(2R,3α)-3-Cyclohexyl-3-trifluoromethylalanyl]-N-(4-amidinobenzyl)-(2S,3R)-2,3-methano-homoprolinamide hydrochloride The expected product is obtained in accordance with the process described in Example 3, starting from the compound described in Example 69.

Elemental Microanalysis:

|  | % C | % H | % N | % Cl |
| --- | --- | --- | --- | --- |
| Calculated: | 55.15 | 6.34 | 11.91 | 6.03 |
| Found: | 55.67 | 6.40 | 11.45 | 6.72 |

EXAMPLE 72

1-[N-Carboxymethyl-(2R,3β)-3-Cyclohexyl-3-trifluoromethylalanyl]-N-(4-amidinobenzyl)-(2S,3R)-2,3-methano-homoprolinamide hydrochloride The expected product is obtained in accordance with the process described in Example 3, starting from the compound described in Example 70.

Elemental Microanalysis:

|  | % C | % H | % N | % Cl |
| --- | --- | --- | --- | --- |
| Calculated: | 55.15 | 6.34 | 11.91 | 6.03 |
| Found: | 55.07 | 6.20 | 11.80 | 6.31 |

EXAMPLE 73

1-[(2R,3α)-3-Cyclohexyl-3-trifluoromethylalanyl]-N-[(6-amino-2-methyl-3-pyridyl)methyl]-(2S,3R)-2,3-methano-homoprolinamide dihydrochloride The expected product is obtained in accordance with the process described in Example 1, starting from the compound described in Step J of Example 69 and the compound described in Preparation E.

EXAMPLE 74

1-[(2R,3β)-3-Cyclohexyl-3-trifluoromethylalanyl]-N-[(6-amino-2-methyl-3-pyridyl)methyl]-(2S,3R)-2,3-methano-homoprolinamide dihydrochloride The expected product is obtained in accordance with the process described in Example 1, starting from the compound described in Step B of Example 70 and the compound described in Preparation E.

EXAMPLE 75

1-[N-Carboxymethyl-(2R,3αa)-3-cyclohexyl-3-trifluoromethylalanyl]-N-[(6-amino-2-methyl-3-pyridyl)methyl]-(2S,3R)-2,3-methano-homoprolinamide dihydrochloride The expected product is obtained in accordance with the process described in Example 3, starting from the compound described in Example 73.

EXAMPLE 76

1-[N-Carboxymethyl-(2R,3β)-3-cyclohexyl-3-trifluoromethylalanyl]-N-[(6-amino-2-methyl-3-pyridyl)methyl]-(2S,3R)-2,3-methano-homoprolinamide dihydrochloride The expected product is obtained in accordance with the process described in Example 3, starting from the compound described in Example 74.

EXAMPLE 77

1-[N-Carboxymethyl-(2R)-leucyl]-N-(4-amidinobenzyl)-(2S,3R)-2,3-methano-homoprolinamide hydrochloride Step A: 1-[(2R)-Leucyl]-N-(4-amidinobenzyl)-(2S,3R)-2,3-methano-homoprolinamide dihydrochloride The expected product is obtained in accordance with the process described in Example 2, starting from the compound described in Preparation B, N-tert-butoxycarbonyl-(2R)-leucine and the compound described in Preparation C.

Step B: 1-[N-Carboxymethyl-(2R)-leucyl]-N-(4-amidinobenzyl)-(2S,3R)-2,3-methano-homoprolinamide hydrochloride The expected product is obtained in accordance with the process described in Example 3, starting from the compound obtained in the above Step.

Elemental Microanalysis:

|  | % C | % H | % N | % Cl |
| --- | --- | --- | --- | --- |
| Calculated: | 57.55 | 7.14 | 14.59 | 7.39 |
| Found: | 57.54 | 7.10 | 14.33 | 8.04 |

EXAMPLE 78

1-[N-Methyl-(2R)-phenylglycyl]-N-(6-amino-2-methyl-3-pyridyl)-methyl]-(2S,3R)-2,3-methano-homoprolinamide dihydrochloride Step A: 1-[(2R)-Phenylglycyl]-N-[(6-amino-2-methyl-3-pyridyl)methyl]-(2S,3R)-2,3-methano-homoprolinamide dihydrochloride The expected product is obtained in accordance with the process described in Example 1, starting from the compound described in Preparation B, N-tert-butoxycarbonyl-(2R)-phenylglycine and the compound described in Preparation E.

Step B: 1-[N-Methyl-(2R)-phenylglycyl]-N-(6-amino-2-methyl-3-pyridyl)methyl]-(2S,3R)-2,3-methano-homoprolinamide dihydrochloride The expected product is obtained in accordance with the process described in Steps B and C of Example 4 starting from the compound described in the above Step.

EXAMPLE 79

1-[N-Benzyl-(2R)-phenylglycyl]-N-(6-amino-2-methyl-3-pyridyl)-methyl]-(2S,3R)-2,3-methano-homoprolinamide dihydrochloride The expected product is obtained in accordance with the process described in Example 5 starting from the compound described in Step A of Example 78.

EXAMPLE 80

1-[(2R)-3-Cyclohexyl-2-hydroxypropionyl]-N-[(6-amino-2-methyl-3-pyridyl)methyl]-(2S,3R)-2,3-methano-homoprolinamide hydrochloride Step A: 1-[(2R)-2-Acetoxy-3-cyclohexylpropionyl]-N-[(6-amino-2-methyl-3-pyridyl)methyl]-(2S,3R)-2,3-methano-homoprolinamide dihydrochloride The expected product is obtained in accordance with the process described in Example 1 starting from the compound described in Step B of Example 2, the compound described in Preparation B and the compound described in Preparation E.

Step B: 1-[(2R)-3-Cyclohexyl-2-hydroxypropionyl]-N-[(6-amino-2-methyl-3-pyridyl)methyl]-(2S,3R)-2,3-methano-homoprolinamide hydrochloride The expected product is obtained in accordance with the process described in Steps D and E of Example 22, starting from the compound described in the above Step.

Elemental Microanalysis:

|  | % C | % H | % N | % Cl |
|---|---|---|---|---|
| Calculated: | 61.25 | 7.82 | 12.42 | 7.86 |
| Found: | 61.66 | 7.76 | 12.29 | 8.43 |

PHARMACOLOGICAL STUDY OF THE COMPOUNDS OF THE INVENTION

EXAMPLE 81

Anti-coagulant Activity, Measurement of Thrombin Time and Activated Cephalin Time in Man In order to evaluate the anti-coagulant activity of the compounds of the invention, the thrombin time (TT) and the activated cephalin time (ACT) were determined in human plasma samples. An $ST_4$ coagulometer (Diagnostica Stago, France) was used. A lyophilised plasma, deficient in platelets (Stago), is taken up in distilled water. The TT is obtained using the reagent Prest Thrombin and the ACT using the reagent PTT Automate Cephalin.

Inhibitor or solvent (10 μl) is added to the plasma (90 μl), which is then incubated for 2 minutes at 37° C. 100 μl of Prest Thrombin (TT) or of PTT Automate Cephalin (ACT) are added and at the same time the stopwatch is started.

Under those condition, the TT is of the order of 18 seconds and the ACT of the order of 12 seconds. The activity of an antagonist is evaluated by its capacity to prolong the TT and the ACT relative to the control. The effect of the inhibitors is expressed by the concentration in μM that doubles the coagulation time ($Ctt_2$).

The compounds of the invention caused very significant prolongation of the coagulation times and the $Ctt_2$ are illustrated in the Table 1 hereinbelow by way of example:

TABLE 1

| Example | TT $C_{tt2}$ (μM) | ACT $C_{tt2}$ (μM) |
|---|---|---|
| 2 | 0.07 | 0.52 |
| 3 | 0.06 | 0.56 |
| 9 | 0.20 | 0.86 |
| 11 | 0.06 | 0.59 |
| 13 | 0.18 | 2.30 |
| 14 | 0.19 | 2.20 |
| 16 | 0.09 | 0.42 |
| 17 | 0.11 | 0.86 |
| 24 | 0.03 | 0.58 |
| 25 | 0.08 | 0.45 |
| 28 | 0.31 | 2.30 |
| 29 | 0.46 | 2.80 |
| 31 | 0.17 | 1.30 |
| 32 | 0.12 | 1.09 |
| 33 | 0.11 | 1.10 |
| 61 | 0.05 | 0.47 |

EXAMPLE 82

Inhibition of Thrombin and of Fibrinolysis Serine Proteases

For in vitro evaluation of the inhibitory activity of the products of the invention on human thrombin (Sigma, specific activity 3230 NIH units/mg), purified human fibrinogen (4 mM, Stago) (Fg) was added to a given amount of thrombin (0.7 nNM) that had previously been incubated with or without the inhibitor to be tested (20° C., 10 minutes).

For in vitro evaluation of the selectivity of the products in respect of plasmin, the same protocol was applied to purified human plasmin (2 nM, Stago), using as substrate a paranitroanilide-containing peptide: <Glu-Phe-Lys-pNA (0.50 mM, S 2403, Kabi).

Inhibitors, enzymes and substrates are diluted in the same buffer (0.01 mM phosphate buffer, pH 7.4, containing 0.12M sodium chloride and 0.05% bovine serum albumin) and then distributed in a polystyrene microtitre plate in a volume of 50 μl. The fibrin formed by the thrombin or by the paranitroanilide released by the action of the serine protease is measured spectrophotometrically at 405 nm after from 15 to 30 minutes' reaction at 20° C.

The Table 2 hereinbelow gives in nM the concentration of the compounds that inhibits 50% of the thrombin enzymatic activity ($IC_{50}$) compared with the control without product. The results obtained demonstrate that the compounds of the invention are potent inhibitors of human thrombin in respect of human fibrinogen.

The Table 3 hereinbelow gives in nM the concentration of the compounds that inhibits 50% of the enzymatic activity ($IC_{50}$) of the fibrinolysis serine proteases. The results obtained show that the compounds exhibit a very significant selectivity in respect of fibrinolysis serine proteases.

TABLE 2

| Example | IC$_{50}$ (nm) |
|---|---|
| 2 | 7.9 |
| 3 | 5.3 |
| 9 | 6.0 |
| 11 | 4.0 |
| 13 | 1.2 |
| 14 | 1.0 |
| 16 | 1.0 |
| 17 | 28.0 |
| 24 | 2.3 |
| 25 | 2.0 |
| 28 | 26.0 |
| 29 | 44.0 |
| 31 | 5.1 |
| 32 | 7.1 |
| 33 | 5.1 |
| 61 | 1.0 |
| 63 | 8.8 |

TABLE 3

| | IC$_{50}$ (nm) | | |
|---|---|---|---|
| Example | Plasmine | t.PA | v.PA |
| 2 | >33000 | 33000 | >33000 |
| 11 | 7200 | >33000 | 2800 |
| 24 | 4700 | 2800 | >33000 |
| 28 | >33000 | >33000 | >33000 |
| 29 | >33000 | >33000 | >33000 |
| 31 | >33000 | >33000 | >33000 |
| 33 | >33000 | >33000 | >33000 |
| 61 | >33000 | 33000 | >33000 |
| 63 | >33000 | >33000 | >33000 |

EXAMPLE 83

Anti-coagulant Activity After Administration Per os to the Dog

Male or female dogs weighing 11–28 kg are treated by the oral route with the products of the invention (5 or 10 mg/kg). The coagulation times (TT, ACT) are determined in dog plasma samples 10 min. before and 30 min., 1 hour, 2 hours, 4 hours and 6 hours after administration of the products. The measurements of the coagulation times are carried out as described in Example 81.

Under the conditions of our experiments, the TT is of the order of 19 seconds and the ACT of the order of 18 seconds.

The substances of the invention significantly increase the TTs and the ACTs in the animals. The Table 4 summarizes the results obtained. The results show the maximal TT and ACT increases which are obtained after the p.o. treatment of the dogs. The values demonstrate the number of times by which the initial time is increased.

TABLE 4

| | TT and ACT increases (number of times by which the initial time is increased) | | |
|---|---|---|---|
| Example | dose (mg/kg) | TT | ACT |
| 2 | 5 | 3.8 | 1.4 |
| 3 | 5 | 8.4 | 2.1 |
| 11 | 5 | 5.6 | 2.3 |
| 17 | 5 | 16.0 | 3.7 |
| 24 | 5 | 6.7 | 1.2 |
| 28 | 10 | 6.2 | 1.8 |
| 29 | 10 | 6.2 | 1.7 |
| 33 | 5 | 7.1 | 1.5 |
| 61 | 5 | 14.2 | 2.0 |

EXAMPLE 84

Pharmaceutical Composition

Formulation for the preparation of 1000 tablets each comprising 10 mg of active ingredient:

| | |
|---|---|
| Compound of Example 1 | 10 g |
| Hydroxypropyl cellulose | 2 g |
| Wheat starch | 10 g |
| Lactose | 100 g |
| Magnesium stearate | 3 g |
| Talc | 3 g |

We claim:

1. A compound selected from those of formula (I):

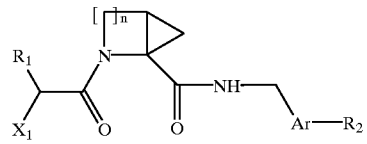

wherein:

n represents 2 or 3,

R$_1$ represents (C$_3$-C$_8$)cycloalkyl, optionally substituted phenyl, or linear or branched (C$_1$-C$_6$)alkyl optionally substituted by one or more identical or different groups selected from halogen, (C$_3$-C$_8$)cycloalkyl, and optionally substituted phenyl, R$_2$ represents:
  amino,
  amidino optionally substituted by one or more identical or different goups selected from linear or branched (C$_1$-C$_6$)alkyl and hydroxy,
  guanidino optionally substituted by linear or branched (C$_1$-C$_6$)alkyl, or
  isothioureido optionally substituted by linear or branched (C$_1$-C$_6$)alkyl, Ar represents aryl or monocyclic nitrogen-containing heteroaryl, X$_1$ represents hydroxy, amino or —NHR$_3$,
  R$_3$ represents propargyl, iminomethyl, linear or branched (C$_1$-C$_6$)alkylsulphonyl, linear or branched aryl(C$_1$-C$_6$)alkylsulphonyl, —CONR'$_3$R"$_3$, or linear or branched (C$_1$-C$_6$)alkyl optionally substituted by:
    —CO$_2$R'$_3$,
    —CONR'$_3$R"$_3$,
    a heterocyclic group,
    aminosulphonyl,
    aryl, or
    heteroaryl, R'$_3$ and R"$_3$, which may be identical or different, each represents hydrogen, linear or branched (C$_1$–C$_6$)alkylsulphonyl, aryl, linear or branched (C$_1$–C$_6$)alkyl optionally substituted by carboxy, linear or branched (C$_1$–C$_6$) alkoxycarbonyl or carbamoyl or form, with the nitrogen atom carrying them, a heterocyclic group, an isomer thereof, and an addition salt thereof with a pharmaceutically/acceptable acid or base, on the understanding that the term "optionally substituted phenyl" means substituted by one or more identical of different groups selected from halogen, linear or branched (C$_1$–C$_6$)alkyl, linear or branched (C$_1$–C$_6$) alkoxy, hydroxy, linear or branched trihalo-(C$_1$–C$_6$) alkyl, and amino optionally substituted by one or more linear or branched (C$_1$–C$_6$)alkyl groups, the term "heterocyclic group" denotes a saturated or unsaturated, mono- or bi-cyclic group having 5 to 12 ring members containing one, two, or three hetero atoms selected from oxygen, nitrogen and sulphur, it being understood that the heterocycle may be optionally substituted by one or more identical or different groups selected from halogen, linear or branched (C$_1$–C$_6$)alkyl, linear or branched (C$_1$–C$_6$)alkoxy, oxo, hydroxy, linear or branched trihalo-(C$_1$–C$_6$)alkyl, and amino optionally substituted by one or more linear or branched (C$_1$–C$_6$)alkyl groups, the term "aryl" means phenyl, biphenylyl, or naphthyl, each of those groups being optionally substituted by one or more identical or different groups selected from halogen, linear or branched (C$_1$–C$_6$)alkyl, linear or branched (C$_1$–C$_6$)alkoxy, hydroxy, linear or branched trihalo-(C$_1$–C$_6$)alkyl, amino optionally substituted by one or more linear or branched (C$_1$–C$_6$)alkyl groups, and carboxy, and the term "heteroaryl group" denotes an aromatic mono- or bicyclic group having 5 to 12 ring members containing one, two or three hetero atoms selected from oxygen, nitrogen and sulphur, it being understood that heteroaryl may be optionally substituted by one or more identical or different groups selected from halogen, linear or branched (C$_1$–C$_6$)alkyl, hydroxy, linear or branched (C$_1$–C$_6$)alkoxy, trihalomethyl, and amino optionally substituted by one or more linear or branched (C$_1$–C$_6$)alkyl groups.

2. Compound of claim 1, wherein R$_1$ represents (C$_3$–C$_8$) cycloalkyl or optionally substituted linear or branched (C$_1$–C$_6$)alkyl.

3. Compound of claim 1, wherein R$_2$ represents amino or amidino.

4. Compound of claim 1, wherein Ar represents optionally substituted phenyl or optionally substituted pyridyl.

5. Compound of claim 1, wherein X$_1$ represents amino or —NHR$_3$, wherein R$_3$ represents linear or branched aryl (C$_1$–C$_6$)alkylsulphonyl or optionally substituted linear or branched (C$_1$–C$_6$)alkyl.

6. Compound of claim 1, which is selected from 1-[(2R)-3,3-diphenylalanyl]-N-(4-amidinobenzyl)-(2S,3R)-2,3-methano-prolinamide, its isomers, and addition salts thereof with a pharmaceutically/acceptable acid.

7. Compound of claim 1, which is selected from 1-[N-carboxymethyl-(2R)-cyclohexylglycyl]-N-(4-amidinobenzyl)-(2S,3R)-2,3-methano-prolinamide, its isomers, and addition salts thereof with a pharmaceutically/ acceptable acid.

8. Compound of claim 1, which is selected from 1-[(2R)-3-cyclohexylalanyl]-N-[(6-amino-2-methyl-3-pyridyl) methyl]-(2S,3R)-2,3-methano-homoprolinamide, its isomers, and addition salts thereof with a pharmaceutically/ acceptable acid.

9. Compound of claim 1, which is selected from 1-[N-methyl-(2R)-3-cyclohexylalanyl]-N-[(6-amino-2-methyl-3-pyridyl)methyl]-(2S,3R)-2,3-methano-homoprolinamide, its isomers, and addition salts thereof with a pharmaceutically/ acceptable acid.

10. Compound of claim 1, which is selected from 1-[(2R)-3,3-diphenylalanyl]-N-(4-amidinobenzyl)-(2S,3R)-2,3-methano-homoprolinamide, its isomers, and addition salts thereof with a pharmaceutically/acceptable acid.

11. Compound of claim 1, which is selected from 1-[(2R)-3,3-dicyclohexylalanyl]-N-[(6-amino-2-methyl-3-pyridyl) methyl]-(2S,3R)-2,3-methano-homoprolinamide, its isomers, and addition salts thereof with a pharmaceutically/ acceptable acid.

12. Method of treating a living body afflicted with a condition requiring a trypsin-related serine protease inhibitor, comprising the step of administering to the living body an amount of a compound of claim 1 which is effective for alleviation of said condition.

13. Pharmaceutical composition useful as a trypsin-related serine protease inhibitor comprising as active principle an effective amount of a compound as claimed in claim 1, together with one or more pharmaceutically acceptable excipients or vehicles.

14. Method of treating a living body afflicted with a condition requiring a thrombin inhibitor, comprising the step of administering to the living body an amount of a compound of claim 1 which is effective for alleviation of said condition.

15. Pharmaceutical composition useful as a thrombin inhibitor comprising as active principle an effective amount of a compound as claimed in claim 1, together with one or more pharmaceutically acceptable excipients or vehicles.

* * * * *

UNITED STATES PATENT AND TRADEMARK OFFICE
CERTIFICATE OF CORRECTION

PATENT NO. : 6,288,077 B1 Page 1 of 1
DATED : September 11, 2001
INVENTOR(S) : Guillaume De Nanteuil It is certified that error appears in the above-identified patent and that said Letters Patent is hereby corrected as shown below:

Title page,
ABSTRACT,
Line 30, please remove the word -- which --.
Line 31, "same/are" should read -- same which are --.

Claims 1, 6, 7, 8, 9, 10 and 11,
"pharmaceutically/acceptable" should read -- pharmaceutically - acceptable --.

Signed and Sealed this

Twenty-sixth Day of February, 2002

Attest:

JAMES E. ROGAN
Attesting Officer
Director of the United States Patent and Trademark Office